US010772524B2

(12) United States Patent
Tsukada et al.

(10) Patent No.: US 10,772,524 B2
(45) Date of Patent: Sep. 15, 2020

(54) BIOMEDICAL ELECTRODE AND WEARABLE ELECTRODE

(71) Applicants: NIPPON TELEGRAPH AND TELEPHONE CORPORATION, Tokyo (JP); TORAY INDUSTRIES, INC., Tokyo (JP)

(72) Inventors: Shingo Tsukada, Atsugi (JP); Nahoko Kasai, Atsugi (JP); Koji Sumitomo, Atsugi (JP); Hiroshi Nakashima, Atsugi (JP); Masanobu Sato, Tokyo (JP); Toru Arakane, Tokyo (JP); Yuri Hamano, Tokyo (JP); Keiji Takeda, Otsu (JP); Noriko Nagai, Otsu (JP); Takashi Teshigawara, Tokyo (JP)

(73) Assignees: NIPPON TELEGRAPH AND TELEPHONE CORPORATION, Tokyo (JP); TORAY INDUSTRIES, INC., Tokyo (JP)

( * ) Notice: Subject to any disclaimer, the term of this patent is extended or adjusted under 35 U.S.C. 154(b) by 304 days.

(21) Appl. No.: 15/577,512

(22) PCT Filed: Jul. 8, 2016

(86) PCT No.: PCT/JP2016/070280
§ 371 (c)(1),
(2) Date: Nov. 28, 2017

(87) PCT Pub. No.: WO2017/007021
PCT Pub. Date: Jan. 12, 2017

(65) Prior Publication Data
US 2018/0146873 A1   May 31, 2018

(30) Foreign Application Priority Data
Jul. 8, 2015   (JP) ................................. 2015-137286

(51) Int. Cl.
*A61B 5/0408*  (2006.01)
*A61B 5/0416*  (2006.01)
(Continued)

(52) U.S. Cl.
CPC .......... *A61B 5/0416* (2013.01); *A61B 5/0408* (2013.01); *A61B 5/0478* (2013.01); (Continued)

(58) Field of Classification Search
CPC ................................... A61B 5/0416
(Continued)

(56) References Cited

U.S. PATENT DOCUMENTS 4,237,886 A * 12/1980 Sakurada ............... A61B 18/16
                                                        252/511
5,157,058 A   10/1992 Dillon et al.
(Continued)

FOREIGN PATENT DOCUMENTS

| CN | 1652826 A   | 8/2005 |
| CN | 101845753 A | 9/2010 |

(Continued)

OTHER PUBLICATIONS

Japanese Office Action regarding JPSN 2017527512, dated Jul. 2, 2019.
(Continued)

*Primary Examiner* — Lee S Cohen
(74) *Attorney, Agent, or Firm* — Harness, Dickey & Pierce, P.L.C.

(57) ABSTRACT

A biomedical electrode which is detachably attached to a garment and includes: an electrode coming into contact with a living body clothed in the garment to acquire a biological signal emitted by the living body; and a locked section which is conductive, is electrically connected to the electrode, is detachably locked to a locking section which is
(Continued)

conductive and is provided in the garment, and is electrically connected to the locking section when locked to the locking section.

8 Claims, 4 Drawing Sheets

(51) Int. Cl.
*A61B 5/0478* (2006.01)
*A61B 5/00* (2006.01)
*A61L 31/06* (2006.01)
*C08J 5/24* (2006.01)

(52) U.S. Cl.
CPC ............ *A61B 5/6804* (2013.01); *A61L 31/06* (2013.01); *C08J 5/24* (2013.01); *A61B 2562/0209* (2013.01); *C08J 2365/00* (2013.01)

(58) Field of Classification Search
USPC ........................................ 600/388, 389, 394
See application file for complete search history.

(56) References Cited

U.S. PATENT DOCUMENTS

| | | | |
|---|---|---|---|
| 2007/0073131 A1* | 3/2007 | Ryu | A41D 13/1281 600/388 |
| 2008/0287770 A1 | 11/2008 | Kurzweil et al. | |
| 2011/0105861 A1 | 5/2011 | Derchak et al. | |
| 2014/0303470 A1 | 10/2014 | Tsukada et al. | |

FOREIGN PATENT DOCUMENTS

| | | |
|---|---|---|
| CN | 103462602 A | 12/2013 |
| EP | 2783725 A1 | 10/2014 |
| JP | H0647012 A | 2/1994 |
| JP | H09122088 A | 5/1997 |
| JP | 2002-159458 A | 6/2002 |
| JP | 2004-513711 A | 5/2004 |
| JP | 3104124 U | 9/2004 |
| JP | 2011-036524 A | 2/2011 |
| JP | 2014-500077 A | 1/2014 |
| JP | 2014-108134 A | 6/2014 |
| JP | 2014-226367 A | 12/2014 |
| JP | 2015-504338 A | 2/2015 |
| JP | 2015-061603 A | 4/2015 |
| JP | 2015-100673 A | 6/2015 |
| WO | WO-02/40091 A2 | 5/2002 |
| WO | WO-2012/066056 A1 | 5/2012 |

OTHER PUBLICATIONS

European Office Action regarding EPSN 168214898, dated Jul. 15, 2019.
ANSI/AAMI EC12:2000 (R2010), "Disposable ECG electrodes", Approved on May 13, 2000 and reaffirmed on Jan. 6, 2005.
International Search Report for PCT/JP2016/070280, ISA/JP, Tokyo, dated Sep. 27, 2016, with translation thereof.
Extended European Search Report in related application EP 16821489.8, EPO, Munich, dated Oct. 24, 2018.
Chinese Office Action regarding application No. 201680037044.9, dated Jun. 18, 2020. Translation attached.

* cited by examiner

BIOMEDICAL ELECTRODE AND WEARABLE ELECTRODE

CROSS-REFERENCE TO RELATED APPLICATIONS

This application is a 371 U.S. National Stage of International Application No. PCT/JP2016/070280, filed Jul. 8, 2016, which claims the benefit of and priority to Japanese Patent Application No. 2015-137286, filed Jul. 8, 2015. The disclosures of the above applications are incorporated herein by reference.

TECHNICAL FIELD

The present invention relates to a biomedical electrode and a wearable electrode.

BACKGROUND ART

Research and development of systems in which biomedical electrodes are attached to undergarment type garments worn by users (living bodies) and biological signals emitted by the users are acquired have been actively underway as effective tools of medical care health systems for aging populations. Hereinafter, an object constituted of biomedical electrodes and garments is referred to as a wearable electrode.

Wearable electrodes require variations in undergarment according to sex, body shape, seasonal adaptations, size development, age, and the like. However, the number of pharmacist certification numbers increases for the various variations, and procedures become complicated due to the various variations, that is, it becomes difficult to approve, manufacture, and manage wearable electrodes as medical instruments. For this reason, the various requirements or the like need to be dealt with using as few wearable electrode variations as possible.

Also, in biomedical electrodes for medical applications, electrodes and wirings are determined by medical standards (for example, refer to Non-Patent Document 1).

DOCUMENTS OF THE PRIOR ART

Patent Document

[Non-Patent Document 1]
ANSI/AAMI EC12:2000 (R2010), "Disposable ECG electrodes"

SUMMARY OF INVENTION

Problems to be Solved by the Invention

However, in the case of single-use (disposable) biomedical electrodes, it is necessary to have a structure in which a biomedical electrode is able to be replaced when washing a garment. In this case, there have been problems with regard to a garment and a biomedical electrode being able to be easily attached to and detached from each other.

The present invention was made in view of the above-described circumstances, and an objective thereof is to provide a biomedical electrode capable of transmitting a biological signal and being easily attached to and detached from a garment and a wearable electrode including such a biomedical electrode.

Means for Solving the Problems

An aspect of the present invention is a biomedical electrode which is detachably attached to a garment, in which the biomedical electrode includes: an electrode coming into contact with a living body clothed in the garment to acquire a biological signal emitted by the living body; and a locked section which is conductive and electrically connected to the electrode, the locked section being detachably locked to a locking section which is conductive and provided in the garment, wherein the locked section is electrically connected to the locking section when locked to the locking section.

As a preferred example, the biomedical electrode includes: a coating member configured to cover the locked section.

Also, at least a part of the locked section may be embedded in the electrode.

As a typical example, the locked section may be a button.
In this case, the button may be typically a male button or a female button of a dot button.

An aspect of the present invention is a wearable electrode including: the biomedical electrode according to any one of the aspects; and the garment, wherein the electrode is formed of a conductive fiber structure which is a fiber structure impregnated with a conductive polymer.

As a preferred example, the conductive fiber structure may be obtained by impregnating the fiber structure with a conductive polymer by applying a liquid dispersion, which is obtained by dispersing the conductive polymer and a binder in a solvent, to the fiber structure.

As a typical example, the conductive polymer may include: a mixture of poly3,4-ethylenedioxythiophene and polystyrene sulfonic acid.

Advantageous Effects of the Invention

According to the present invention, a biomedical electrode and a wearable electrode capable of transmitting a biological signal and being easily attached to and detached from a garment can be provided.

EMBODIMENTS FOR CARRYING OUT THE INVENTION

An embodiment of a wearable electrode according to the present invention will be described below with reference to FIGS. 1 to 6.

Figure 1:
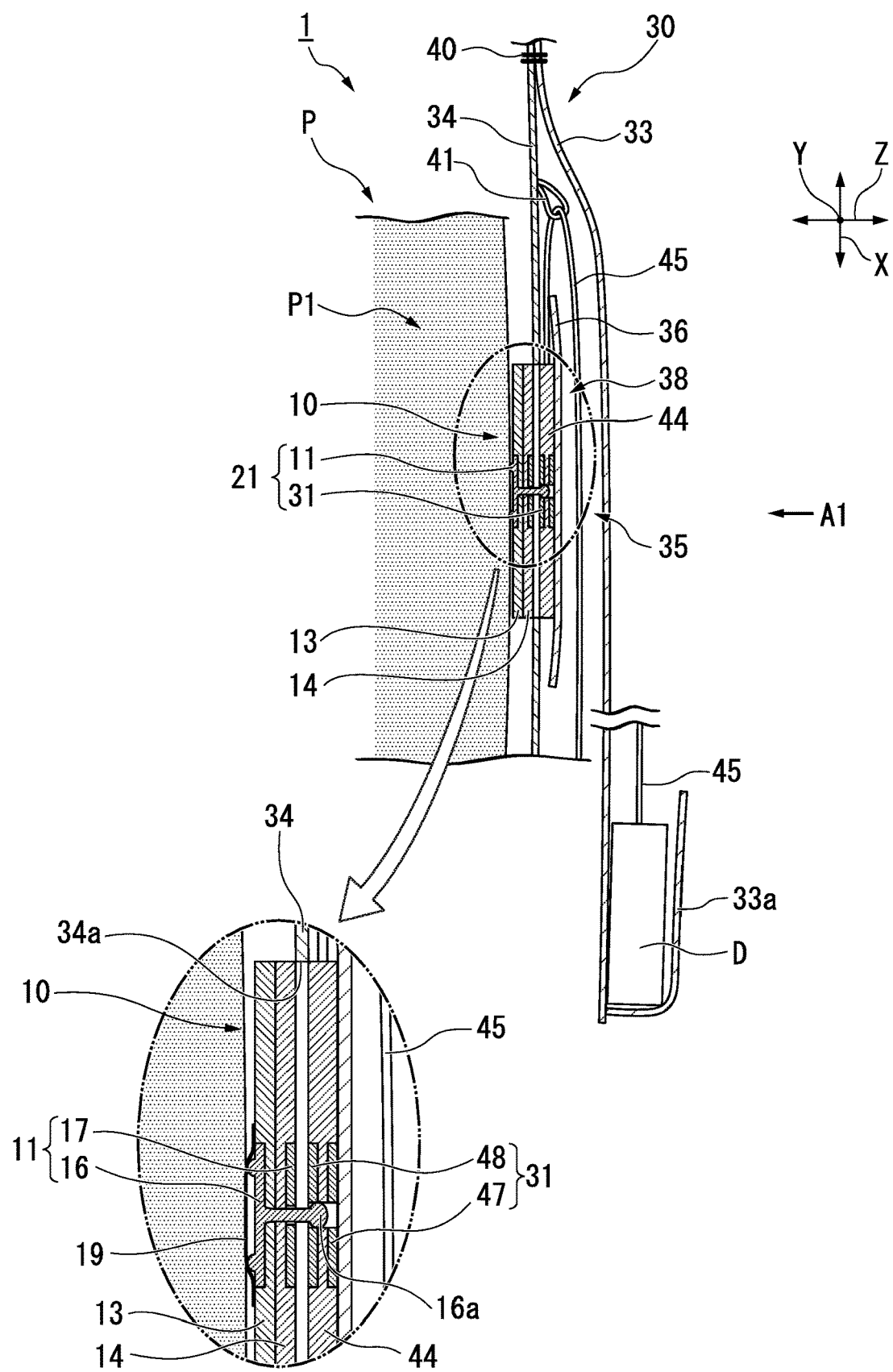
FIG. 1 is a vertical cross-sectional view with respect to a front surface of a wearable electrode according to an embodiment of the present invention.
Figure 2:
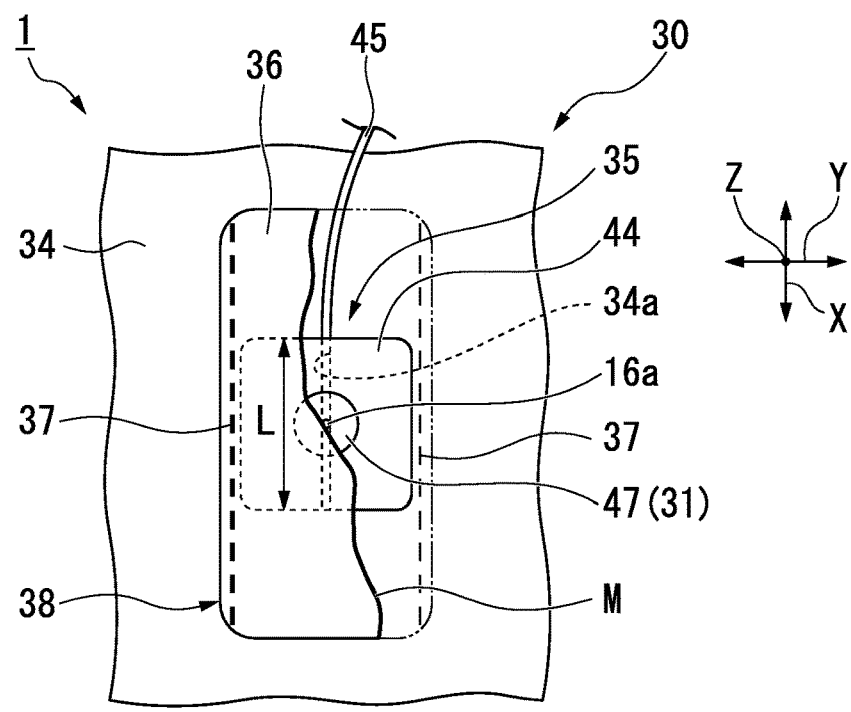
FIG. 2 is a diagram viewed in a direction indicated by an arrow A1 in FIG. 1.

As shown in FIGS. 1 and 2, a wearable electrode 1 according to the embodiment includes a biomedical electrode 10 having a male button (a locked section; a button) 11 and an undergarment (a garment) 30 having a female button (a locking section) 31 which is detachably locked to the male button 11. Note that a dot button (a snap button) 21 is constituted of the male button 11 and the female button 31.

FIG. 1 illustrates a state in which a standing user (a living body) P is clothed in the wearable electrode 1. In FIG. 2, an outer member 33 which will be described below is not illustrated and a reinforcing fabric 36, a part of which is cut along a break line M, is illustrated.

First, the biomedical electrode 10 will be described below.

Figure 3:
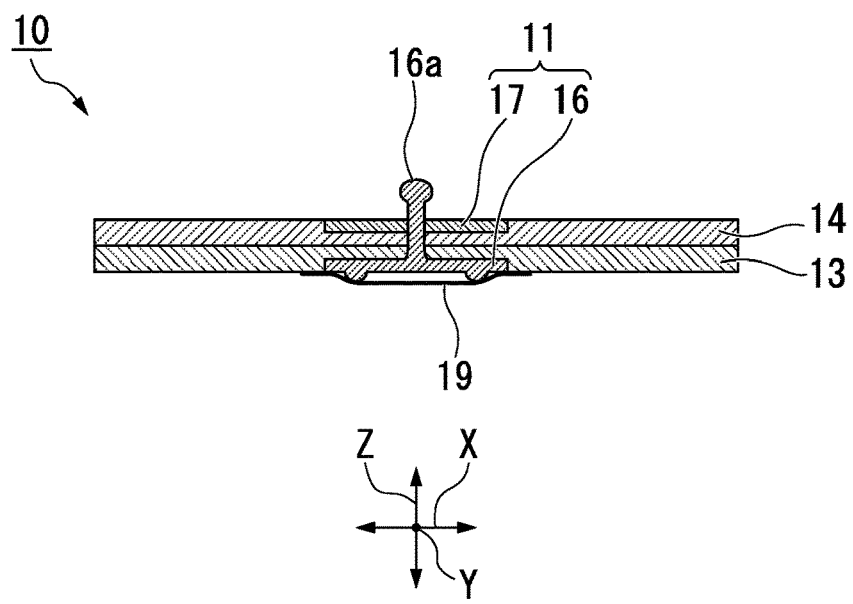
FIG. 3 is a cross-sectional view of a biomedical electrode of the wearable electrode.
Figure 4:
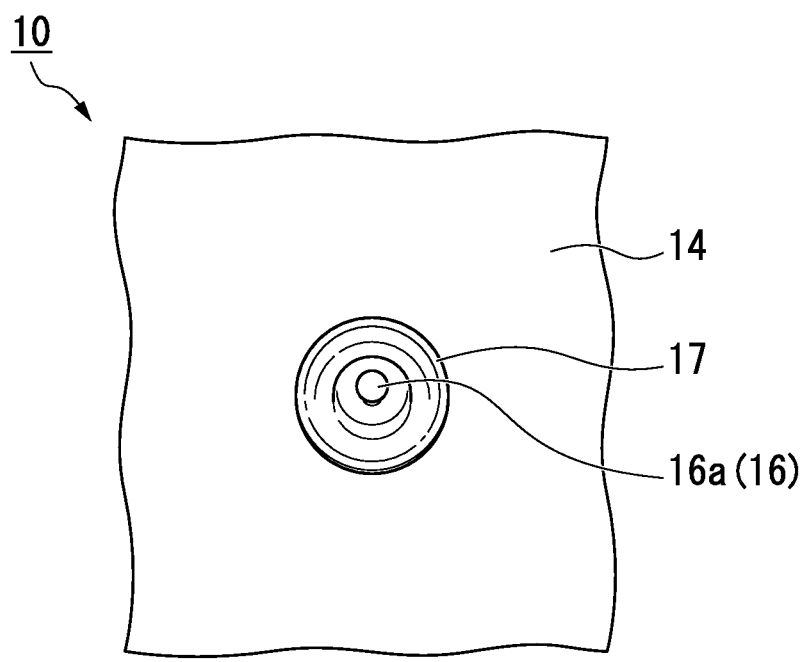
FIG. 4 is a plan view of a main part of the biomedical electrode.
Figure 5:
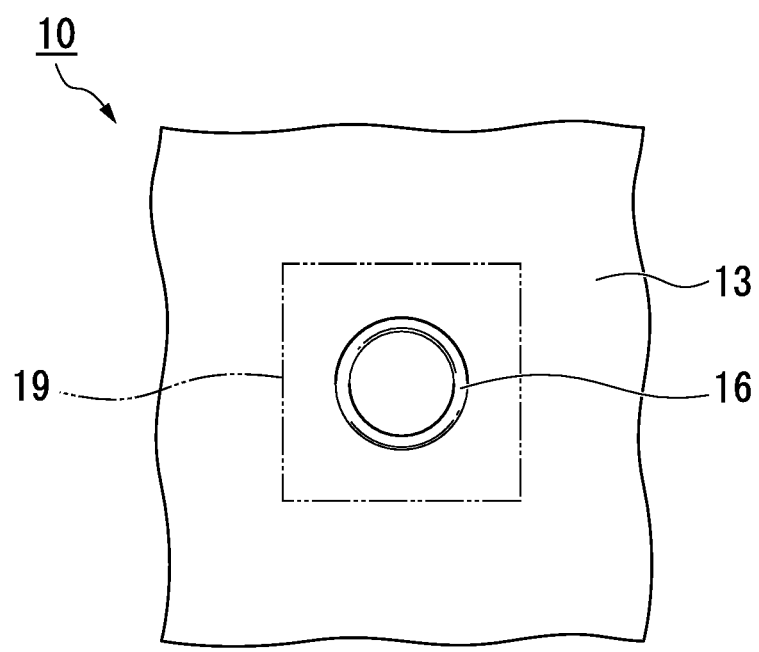
FIG. 5 is a bottom view of the main part of the biomedical electrode.

As shown in FIGS. 3 to 5, the biomedical electrode 10 according to the embodiment includes an electrode 13 formed in a flat plate shape, a waterproof layer 14 stacked on the electrode 13, and the above-described male button 11 fixed to the electrode 13 and a waterproof layer 14. Note that, in FIG. 5, a cover 19 which will be described below is indicated by an alternate long and two short dashed line.

The electrode 13 is formed of a conductive fiber structure obtained by impregnating a fiber structure as foundation cloth serving as cloth which is a base thereof with conductive polymers.

Examples of a form of the fiber structure used for the electrode 13 include woven fabrics, knitted fabrics, and nonwoven fabrics. When the amount of conductive resins (conductive polymers) to be impregnated into the fiber structure is insufficient, since washing durability in repeated use is not obtained, a base weight of the fiber structure (a unit weight of the foundation cloth) is preferably 50 g/m$^2$ or more and 300 g/m$^2$ or less. When the base weight is less than 50 g/m$^2$, the amount of the impregnated conductive resin decreases and thus washing durability cannot be obtained. When the base weight is more than 300 g/m$^2$, the wearability is worse. The base weight is more preferably 60 g/m$^2$ or more and 250 g/m$^2$ or less.

The thickness of the fiber structure is preferably 0.2 mm or more and 2.0 mm or less. When the thickness is less than 0.2 mm, since the cloth is too thin, a substantial based weight decreases and thus the amount of the impregnated conductive resin decreases. When the thickness exceeds 2.0 mm, since the cloth is too thick, the wearability is worse. The thickness is more preferably 0.3 mm or more and 1.5 mm or less.

Also, in order to continuously obtain good electrocardiographic waveforms, it is necessary to bring the electrode 13 into contact with skin and maintain an attached state. Since cloth constituting a fiber structure needs to have flexibility in order for the electrode 13 to be continuously attached to skin, the fiber structure is preferably a woven fabric, a knitted fabric, or a nonwoven fabric, and more preferably a knitted fabric having higher flexibility. Here, when the electrode 13 is broken or moves during wear because the electrode 13 itself is too flexible, a member for reinforcement may be disposed on a back side of the electrode 13.

In addition, tissues and manufacturing methods of fiber structures represented by knitted fabrics are not particularly limited, but a shape of the electrode 13 is preferably a shape which retains moisture such as sweat and double knits can be preferably used as the knitted fabric. Examples of such tissues include double raschel tissues, cardboard tissues, reversible tissues, smooth tissues, milling tissues, fleeced tissues, and the like, but the present invention is not limited thereto.

Woven or knitted fabrics used for the electrode 13 of the present invention preferably include multifilament yarns composed of a plurality of monofilaments in view of supporting of a conductive resin in a fiber structure and high conductivity. Fineness of the multifilament yarns is not particularly limited, but the fineness thereof is preferably 30 dtex to 400 dtex in view of taking advantage of characteristics of the fiber structure. The mixing ratio of multifilament yarns in the woven or knitted fabric is not particularly limited as long as the mixing ratio does not affect performance of the fiber structure, but the mixing ratio thereof is preferably a higher mixing ratio in view of conductivity and durability and more preferably 50% or more and 100% or less.

Examples of materials of the multifilament yarn used for the woven or knitted fabric include polyester synthetic fibers such as polyethylene terephthalate, polytrimethylene terephthalate, and polybutylene terephthalate, and polyamide-based synthetic fibers such as nylon, and the like, but the present invention is not limited thereto. Furthermore, materials obtained by blending additives such as titanium oxide into the woven or knitted fabric may be used and fibers modified with polymers used to give functionality such as hygroscopicity improvement may also be used.

Also, cross-sectional shapes of unit monofilaments constituting multifilaments are not limited, and yarns with various different cross-sectional shapes represented by circular shapes, triangular shapes, octagonal shapes, flat shapes, and Y shapes can also be used. As non-elastic yarns, core sheaths or side-by-side type composite yarns composed of polymers with different viscosities can also be used. False twisted yarns obtained by performing false twisting on raw yarns may also be used. Synthetic fibers of polyacrylonitrile, polypropylene, and the like, regenerated fibers of rayon, polynosic, cupra, and the like, semisynthetic fibers of acetate, triacetate, and the like, and natural fibers represented by silk can be used.

The fiber structure according to the present invention preferably includes multifilaments composed of monofilaments with filament diameters of 0.2 dtex or less in view of supporting of conductive resins on fiber surfaces and in voids between fibers. The mixing ratio of the monofilament multifilaments of 0.2 dtex or less in the fiber structure is not particularly limited as long as the mixing ratio does not affect performance of the fiber structure, but the mixing ratio is preferably a high mixing ratio in view of conductivity and durability and more preferably 50% or more and 100% or less.

In addition, as the number of monofilaments increases, voids formed by a plurality of monofilaments, that is, the sizes of portions carrying conductive resins, decrease, so that performance of supporting conductive resins in a fiber structure increases and excellent high conductivity and washing durability can be obtained because continuity of conductive resins is maintained even when the sizes of portions carrying conductive resins are decreased by decreasing filament diameters.

Microfibers with filament diameters of 5 μm or less used for artificial leathers, outer materials, or the like are preferably used, and nanofibers with filament diameters of 10 nm or more and 1000 nm or less that have been used in recent years for the purpose of preventing slipping of linings of sports clothes, brassieres, golf gloves, and the like are more preferably used.

Fiber structures including nanofiber staple yarn assemblies prepared from "Nanoalloy (registered trademark)" fibers, monofilament yarn assemblies prepared using an electrospinning method and the like, and nanofibers prepared using a known method can be appropriately used for nanofibers, but fiber structures including multifilament yarns of nanofibers are more desirable.

The multifilament yarns of the nanofibers can be prepared using a known composite spinning method or the like.

For example, nanofiber multifilament yarns, in which variations in filament diameters are small, obtained by performing sea component removal treatment on composite fibers using a composite spinneret disclosed in Japanese Examined Patent Application, First Publication No. 2013-185283 can be effectively used, but the present invention is not limited thereto. Here, the sea component removal treatment refers to a process of melting sea components of fibers and leaving island components.

As the conductive polymer, conductive polymers containing a mixture of poly3,4-ethylenedioxythiophene and polystyrene sulfonic acid (PEDOT-PSS) can be appropriately used.

Besides this, examples of the conductive polymers include pyrrole-based, thiophene-based, isothianaphthene-based, phenylene-based, acetylene-based, and aniline-based conductive polymers, copolymers thereof, or the like. In addition, examples of dopants of the conductive polymers may be at least one type of ion of polymer ions such as halide ions, perchlorate ions, tetrafluoroborate ions, hexafluoroarsenate ions, sulfate ions, nitrate ions, thiocyanate ions, phosphate ions, trifluoroacetate ions, tosylate ions, alkylsulfonate ions, and polyacrylate ions.

The electrode 13 having the fiber structure according to the present invention has low irritation and high safety when in contact with skin. When a signal cannot be satisfactorily obtained due to drying of skin or the like, it is desirable to apply a small amount of physiological saline or humectant to the fiber structure. Examples of the humectant include glycerol, sorbitol, polyethylene glycol, polyethylene glycol-polypropylene glycol copolymers, ethylene glycol, sphingosine, phosphatidylcholine, and the like, and one of these may be independently used or two or more of these may be used in combination.

By moisturizing the electrode 13 as described above, when the electrode 13 comes into contact with skin of a user P, an adhesive force occurs due to wettability of the humectant.

More specifically, the electrode 13 is obtained by impregnating the fiber structure with a conductive polymer by applying a liquid dispersion, which is obtained by dispersing the above-described conductive polymer and a binder in a solvent, to the above-described fiber structure.

The type of solvent is not particularly limited and is appropriately selected in accordance with types and purposes of conductive polymers or binders.

The conductive polymer is used with a binder to increase scratch resistance or a surface hardness of a coating film containing conductive polymer and improve adhesion to a base material. Furthermore, with use of the binder, it becomes easy to support the conductive polymer on a fiber structure and thus increase in surface resistance after an electrode member has been subjected to repeated washing can also be minimized.

A binder may be a thermosetting resin or a thermoplastic resin. Examples of the binder include: polyesters such as polyethylene terephthalate, polybutylene terephthalate, and polyethylene naphthalate; polyimides; polyamide imides; polyamides such as polyamide 6, polyamide 6,6, polyamide 12, and polyamide 11; fluororesins such as polyvinylidene fluoride, polyvinyl fluoride, polytetrafluoroethylene, ethylene tetrafluoroethylene copolymers, and polychlorotrifluoroethylene; vinyl resins such as polyvinyl alcohol, polyvinyl ether, polyvinyl butyral, polyvinyl acetate, and polyvinyl chloride; epoxy resins; xylene resins; aramid resins; polyimide silicones; polyurethanes; polyureas; melamine resins; phenol resins; polyethers; acrylic resins; copolymers thereof, and the like.

Such a binder may be dissolved in an organic solvent, may be subject to a reaction with a functional group such as a sulfonic acid group or a carboxylic acid group to form an aqueous solution, and may be dispersed in water through emulsification or the like.

Among binder resins, one or more of polyurethanes, polyester, acrylic resins, polyamide, polyimide, epoxy resins, and polyimide silicones are desirable because these binder resins can be easily mixed in. The solvent to be used is not limited as long as the solvent can stably disperse a conductive polymer and a binder, but water or a mixed solution of water and alcohol can be appropriately used. When a polythiophene-based conductive polymer such as PEDOT-PSS is used, it is desirable to use a mixed solvent of water and ethanol.

The size or a shape of the electrode 13 is not particularly limited as long as a biological signal can be detected and vertical and horizontal lengths are preferably 2 cm or more and 20 cm or less. When the vertical and horizontal lengths of the electrode 13 are less than 2 cm, since an area of the electrode 13 is too small, the electrode 13 is also easily deviated and easily picks up noise when garments move during exercise or the like. When the vertical and horizontal lengths thereof exceed 20 cm, since it is not the size required for actual signal detection and the area of the electrode 13 is too large, an interval between neighboring electrodes is small, which easily causes trouble such as short-circuiting.

Figure 6:
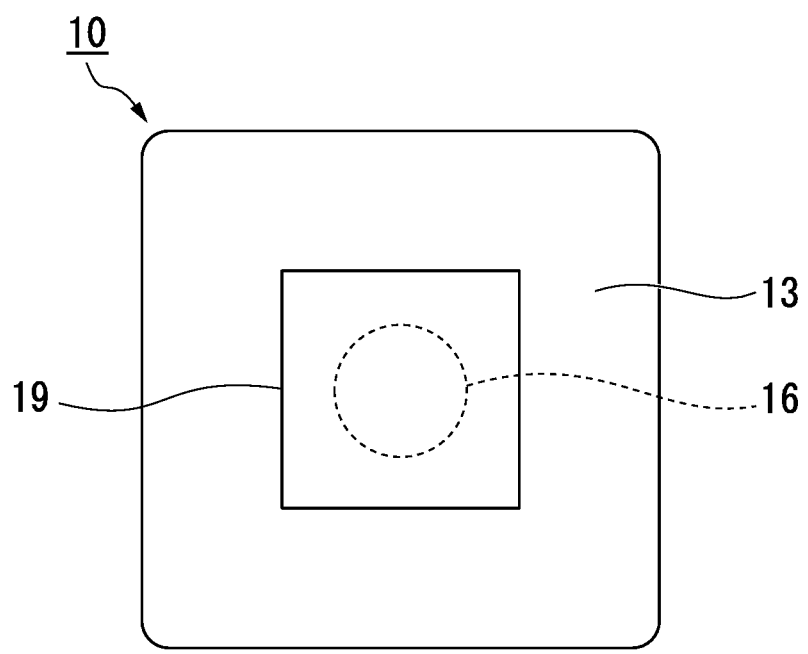
FIG. 6 is a bottom view of the biomedical electrode.

The vertical and horizontal lengths thereof are more preferably 2.5 cm or more and 18 cm or less. As shown in FIG. 6, for example, an electrode having a square shape of about 4 cm×about 4 cm and a shape with rounded corners is more preferably used.

The waterproof layer 14 is a layer through which liquid moisture does not pass.

The waterproof layer 14 mentioned herein is not necessarily required and is preferably stacked on one surface of a fiber structure containing a conductive substance as a resin layer. It is desirable to stack a resin layer on a back surface side of a surface coming into contact with a skin side of a fiber structure used for the electrode 13 in consideration of applications to a living body electrode. When a biological signal is detected, it is difficult to detect the biological signal stably when the electrode 13 dries.

Therefore, because it is necessary to maintain the electrode 13 in a wet state to some extent, one surface of the electrode 13 is covered with a resin layer so that drying thereof can be prevented and thus conductivity can be stably obtained. In addition, one surface of the electrode 13 is covered with a resin layer so that falling-off of a conductive resin during washing can be reduced and thus washing durability can be significantly improved.

The type and the shape of a polymer constituting the resin layer are not particularly limited as long as the polymer is a polymer through which a liquid does not pass, and for example, a method of laminating a polymer film of acryl, vinyl chloride, or the like, a method of coating acrylic resins or urethane resins, and the like can be provided. Although a polymer layer is not particularly limited, when it is necessary to moderately control a feeling of stickiness in the skin, the polymer layer is preferably a waterproof moisture-permeable layer.

Examples of the waterproof moisture-permeable layer include forms obtained by stacking polytetrafluoroethylene (PTFE) porous membranes, non-porous membranes made of hydrophilic elastomers such as hydrophilic polyester resins and polyurethane resins, polyurethane resin microporous membranes, or the like, known membranes, films, stacked articles, resins or the like using a coating or laminating method, but the present invention is not limited thereto. The waterproof layer 14 is preferably bonded in a stacked manner by laminating a polyurethane resin microporous membrane with elasticity in view of followability to a fiber structure which is a base material. In addition, in order to improve moisture permeability, microporosity may be formed in a fiber structure obtained by stacking a resin layer on one surface thereof using a punching machine or a sewing machine.

The male button 11 has a known constitution and includes a post 16 and a stud 17 as illustrated in the enlarged diagram in FIG. 1. The post 16 and the stud 17 are formed of metals which are conductive such as stainless steel. The post 16 is disposed on the electrode 13 side and the stud 17 is disposed on the waterproof layer 14 side. A part of the post 16 is embedded in the electrode 13 and a part of the stud 17 is embedded in the waterproof layer 14. For this reason, a step formed by the electrode 13 and the post 16 and a step formed by the waterproof layer 14 and the stud 17 decrease.

A head section 16a of the post 16 protrudes to the outside via the stud 17. The post 16 and the stud 17 are electrically connected to each other. The male button 11 is provided on center portions of the electrode 13 and the waterproof layer 14, but installation positions of the male button 11 is not particularly limited. The male button 11 is electrically connected to the electrode 13.

The male button 11 is mechanically connected to the undergarment 30 and the biomedical electrode 10, supports a center portion of the biomedical electrode 10 at one point, and electrically connects the biomedical electrode 10 to a measuring device (a processing device) D via a female button 31.

The post 16 of the male button 11 is preferably covered with the cover (a coating member) 19.

The cover 19 is not particularly limited as long as the post 16 does not come into direct contact with the user P, but seam tapes or the like which are usually used for clothes can be used. Note that, although it is assumed that the coating member is the cover 19, the coating member may be a coating or the like configured to cover an outer surface of the post 16 in contact with the user P.

As shown in FIGS. 1 and 2, the undergarment 30 includes the outer member 33, a backing member 34 connected to the outer member 33, and a wiring section 35 provided in the backing member 34. The outer member 33 and the backing member 34 can be formed desired fabrics or the like. A slit 34a extending in a vertical direction is formed in the backing member 34. The slit 34a passes through the backing member 34 in a thickness direction. A length L of the slit 34a in the vertical direction is preferably shorter than a length of a short side of the biomedical electrode 10. For example, when the biomedical electrode 10 is a 4 cm square, the length thereof is less than 4 cm (refer to FIG. 2). The width of the slit 34a is not particularly limited as long as the head section 16a of the post 16 is movable along the slit 34a, but a width of the slit 34a is preferably about an outer circumference of the head section 16a.

The slit 34a is preferably formed in a position facing a chest P1 of the user P when the user P is clothed in the wearable electrode 1.

The reinforcing fabric 36 may be provided between the backing member 34 and the outer member 33. For example, the reinforcing fabric 36 is formed in a rectangular shape using a desired fabrics or the like. The reinforcing fabric 36 is disposed to cover the slit 34a of the backing member 34. The backing member 34 and the reinforcing fabric 36 are connected, for example, by a pair of stitches 37 formed by stitching the backing member 34 and the reinforcing fabric 36 using threads. The stitches 37 extend in a vertical direction. The backing member 34, the slit 34a, the reinforcing fabric 36, and the pair of stitches 37 configured in this way constitute tubular structure 38.

The outer member 33 and the backing member 34 are connected to a connection section 40 such as stitches provided above the reinforcing fabric 36. As will be described below, the biomedical electrode 10 is attached to the backing member 34 via the slit 34a. It is assumed that a part which is closest to the slit 34a in a part to which the backing member 34 and the outer member 33 are connected is the connection section 40. The connection section 40 is away from the slit 34a of the backing member 34 and the separated distance is preferably 1 cm or more. This is because movement of the outer member 33 is not easily transferred to the biomedical electrode 10 via the connection section 40 as will be described below.

An annular loop section 41 may be attached to a part above the reinforcing fabric 36 in the backing member 34.

The wiring section 35 includes a support plate 44 disposed in the tubular structure 38, the female button 31, which have been described above, fixed to a center portion of the support plate 44, and a connection wiring 45 having a first end portion connected to the female button 31.

The support plate 44 is formed in a rectangular shape using a desired resinous plate material, fabric, or the like. The support plate 44 preferably has certain rigidity to be able to easily move in the tubular structure 38. A width of the support plate 44 is shorter than a distance between the pair of stitches 37. The support plate 44 is vertically movable in the tubular structure 38 using the pair of stitches 37 as guides.

The position of the support plate 44 in a vertical direction is maintained by a frictional force occurring between the support plate 44 and the backing member 34 and the reinforcing fabric 36.

The female button 31 is of a known constitution provided in the undergarment 30 and includes a head 47 and a socket 48. The head 47 and the socket 48 are formed of metals which are conductive such as stainless steel. The head 47 is disposed on the reinforcing fabric 36 side and the socket 48 is disposed on the backing member 34 side. The head 47 and the socket 48 are electrically connected to each other.

The head section 16a of the male button 11 via the slit 34a of the backing member 34 can be locked to the female button 31. The female button 31 and the male button 11 of the biomedical electrode 10 disposed to sandwich the slit 34a are locked to each other to be integrated and vertically move along the slit 34a. Thus, the position of the biomedical electrode 10 in the vertical direction with respect to the chest P1 is optimized and a biological signal can be measured.

When the male button 11 and the female button 31 are locked to each other, the male button 11 and the female button 31 are electrically connected together.

As the connection wiring 45, a well-known wiring such as a so-called flexible wiring in which the wiring is soft can be appropriately selected and used. Discomfort of the user P experiencing due to a local load applied to the chest P1 can be suppressed using the flexible wiring.

A core wire (not shown) of the connection wiring 45 is electrically connected to the female button 31. The connection wiring 45 is drawn upward from the female button 31, passes through the loop section 41, and then is routed downward. A second end portion of the connection wiring 45 is connected to the measuring device D.

The measuring device D has a known constitution capable of processing an electric biological signal emitted by the user P.

For example, the measuring device D is held in an accommodation section 33a such as a pocket provided in the outer member 33. The measuring device D may be held in an accommodation section provided in the backing member 34, a waist bag attached to the user P, or the like.

An action of the wearable electrode 1 configured as described above will be described below.

The user P performs washing or the like of the undergarment 30 obtained by removing the biomedical electrode 10. A wearable electrode 1 is constituted by locking the male button 11 of the washed biomedical electrode 10 to the female button 31 of the undergarment 30.

At this time, the female button 31 and the male button 11 are electrically connected to each other.

When the user P is clothed in the undergarment 30 of the wearable electrode 1, the electrode 13 of the biomedical electrode 10 comes into contact with the skin of the chest P1 of the user P. Since the electrode 13 is easily deformed, the electrode 13 is easily deformed in accordance with a shape of the chest P1 and a biological signal emitted by the user P is easily acquired by the electrode 13.

Since the cover 19 is provided on the biomedical electrode 10, the male button 11 does not come into direct contact with the chest P1 and thus the user P is less likely to feel uncomfortable against the biomedical electrode 10 in contact with the chest P1.

Since moisture passes through the waterproof layer 14 when the waterproof layer 14 is set to be a waterproof moisture-permeable layer, the chest P1 is not easily warmed up.

The sticking effect of the biomedical electrode 10 to skin due to wettability and viscosity thereof is stabilized when the following four conditions are satisfied. Firstly, the biomedical electrode 10 is brought into contact with skin in parallel (flat). Secondly, the biomedical electrode 10 is supported at a center portion of the biomedical electrode 10 and is pressed toward skin. Thirdly, the biomedical electrode 10 is not deviated (not shifted) on skin. Fourthly, humectants is not let be lost (by dry diffusion or the like).

Examples of factors causing failure or interruption of measurement due to the loss of the above-described four conditions include a force (horizontal and vertical forces) of peeling off the biomedical electrode 10 from a skin surface, skin deformation due to movement of a body, and loss of humectants (due to drying or the like). The force of peeling off the biomedical electrode 10 and the skin deformation due to the movement of the body lead to poor contact between skin and the biomedical electrode 10. Loss of humectants leads to an increase in contact resistance. Particularly, measurement is impaired due to large movement of his or her body, the connection wiring 45 of the biomedical electrode 10, and pulling by an undergarment in the related art in many cases.

The user P appropriately moves the biomedical electrode 10 in a vertical direction according to necessity to adjust a position of the biomedical electrode 10.

A biological signal acquired by the electrode 13 of the biomedical electrode 10 is transmitted to the measuring device D via the male button 11, the female button 31, and the connection wiring 45 which are electrically connected to each other.

When the measuring device D starts up, measurement of biological signals of electrodcardiographic waveforms or the like is started. The user P performs an operation such as walking while measuring an electrocardiogram.

The outer member 33 of the undergarment 30 moves along with the user P's motion in some cases. Since the connection section 40 is away from the slit 34a of the backing member 34, movement of the outer member 33 is hardly transferred to the slit 34a of the backing member 34 via the connection section 40. For this reason, a state in which the electrode 13 of the biomedical electrode 10 comes into contact with the chest P1 of the user P is maintained.

When the connection wiring 45 serving as a part near the measuring device D is pulled, a force acting on the connection wiring 45 is received by the loop section 41 and then transmitted to the female button 31. Thus, a force pulling the connection wiring 45 is suppressed from being directly transmitted to the female button 31.

As described above, according to the biomedical electrode 10 and the wearable electrode 1 of the embodiment, the biomedical electrode 10 can be easily attached to and detached from the undergarment 30 due to the male button 11 and the female button 31. Furthermore, a biological signal acquired by the electrode 13 in contact with the user P can be transmitted to the female button 31 via the male button 11.

The center portion of the biomedical electrode 10 is supported by the female button 31 on the undergarment 30 side. The dot button 21 can press the biomedical electrode 10 toward skin while maintaining electrical contact to the biomedical electrode 10 and thus can keep a state in which the electrode 13 of the biomedical electrode 10 is attached to the skin.

Also, since a stable contact state to skin can be maintained as long as an adhesive force between the electrode 13 and the chest P1 is not lost, long-term measurement of a biological signal is possible.

The biomedical electrode 10 includes the cover 19 so that the user P is less likely to feel uncomfortable and discomfort against the biomedical electrode 10 in contact with the chest P1. The biomedical electrode 10 reduces a local load applied to the user P's body so that the user P has almost no uncomfortable during wearing and thus long-term measurement can be performed.

A part of the male button 11 is embedded in the electrode 13 so that a step formed by the electrode 13 and the male button 11 decreases. Therefore, the user P in contact with the electrode 13 is less likely to feel uncomfortable.

The electrode 13 is formed of a conductive fiber structure which is a fiber structure obtained by impregnating conductive polymers. For this reason, the electrode 13 is easily deformed in accordance with the shape of the chest P1 so that the electrode 13 can reliably acquire a biological signal from the chest P1.

Although the embodiment of the present invention has been described in detail above with reference to the drawings, a specific constitution is not limited to such an embodiment and also includes a design or the like within the scope which does not depart from the gist of the present invention.

For example, in the embodiment, it is assumed that a locked section is the male button 11 and a locking section is the female button 31. However, it may be assumed that a locked section is a female button and a locking section is a male button.

It is assumed that a locking section and a locked section corresponds to the dot button 21. However, a locking section and a locked section may be other connection structures, buttons, or the like such as a snap fit as long as the locking section and the locked section which is conductive and are easily attached and detached.

In the embodiment, it is assumed that the measuring device D configured to display an electrocardiogram is electrically connected to the female button 31 via the connection wiring 45. However, a device connected to the female button 31 is not limited thereto and may be, for example, a device capable of performing processing such as detection and display of a biological signal and a device configured to transmit a biological signal to an external device through wireless communication or the like.

INDUSTRIAL APPLICABILITY

According to the present invention, a biomedical electrode and a wearable electrode capable of transmitting a biological signal and being easily attached to and detached from a garment can be provided.

REFERENCE SYMBOLS

1 Wearable electrode
10 Biomedical electrode
11 Male button (locked section)
13 Electrode
19 Cover (coating member)
21 Dot button
30 Undergarment (garment)
31 Female button (locking section)

The invention claimed is:

1. A biomedical electrode which is detachably attached to a garment, the biomedical electrode comprising:
   an electrode coming into contact with a living body clothed in the garment to acquire a biological signal emitted by the living body;
   a locked section which is conductive and electrically connected to the electrode, the locked section being detachably locked to a locking section which is conductive and provided in the garment, wherein the locked section is electrically connected to the locking section when locked to the locking section;
   a connection wiring electrically connected to the locking section; and
   a loop section provided on the garment such that the loop section is spatially separated and disposed vertically from the locking section, the connecting wiring passing through the loop section.

2. The biomedical electrode according to claim 1, comprising a coating member configured to cover the locked section.

3. The biomedical electrode according to claim 1, wherein at least a part of the locked section is embedded in the electrode.

4. The biomedical electrode according to claim 1, wherein the locked section is a button.

5. The biomedical electrode according to claim 4, wherein the button is a male button or a female button of a dot button.

6. A wearable electrode comprising:
   the biomedical electrode according to claim 1
   wherein the electrode is formed of a conductive fiber structure which is a fiber structure impregnated with a conductive polymer.

7. The wearable electrode according to claim 6, wherein the conductive fiber structure is obtained by impregnating the fiber structure with a conductive polymer by applying a liquid dispersion, which is obtained by dispersing the conductive polymer and a binder in a solvent, to the fiber structure.

8. The wearable electrode according to claim 6, wherein the conductive polymer includes a mixture of poly3,4-ethylenedioxythiophene and polystyrene sulfonic acid.

* * * * *